United States Patent
Pelssers et al.

(10) Patent No.: US 8,770,049 B2
(45) Date of Patent: Jul. 8, 2014

(54) SAMPLING DEVICE AND SAMPLING METHOD

(75) Inventors: Eduard Gerard Marie Pelssers, Panningen (NL); Jeroen Hans Nieuwenhuis, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 206 days.

(21) Appl. No.: 13/000,728

(22) PCT Filed: Jun. 22, 2009

(86) PCT No.: PCT/IB2009/052668
§ 371 (c)(1),
(2), (4) Date: Dec. 22, 2010

(87) PCT Pub. No.: WO2010/001296
PCT Pub. Date: Jan. 7, 2010

(65) Prior Publication Data
US 2011/0100104 A1    May 5, 2011

(30) Foreign Application Priority Data

Jul. 4, 2008    (EP) .................................... 08104632

(51) Int. Cl.
*G01N 1/02* (2006.01)
*A61B 10/00* (2006.01)
*B01L 3/00* (2006.01)
*G01N 1/10* (2006.01)

(52) U.S. Cl.
CPC ....... *B01L 3/502715* (2013.01); *B01L 2200/10* (2013.01); *A61B 10/0045* (2013.01); *B01L 3/5029* (2013.01); *B01L 2400/0481* (2013.01); *B01L 2200/027* (2013.01); *B01L 2400/0406* (2013.01); *B01L 2300/0816* (2013.01); *G01N 2001/028* (2013.01); *B01L 2200/16* (2013.01); *B01L 2300/0636* (2013.01)
USPC ........ 73/864.72; 422/411; 422/412; 422/413; 422/419; 73/64.56; 73/61.41; 73/864.71; 73/863.31

(58) Field of Classification Search
USPC ...................................................... 73/864.71
See application file for complete search history.

(56) References Cited

U.S. PATENT DOCUMENTS

| | | |
|---|---|---|
| 4,963,325 A | 10/1990 | Lennon et al. |
| 4,978,504 A | 12/1990 | Nason |
| 6,248,598 B1 | 6/2001 | Bogema |
| 6,372,516 B1 * | 4/2002 | Sun ............................... 436/518 |

(Continued)

FOREIGN PATENT DOCUMENTS

| | | |
|---|---|---|
| EP | 1566640 A1 | 8/2005 |
| GB | 2432420 A | 5/2007 |

(Continued)

*Primary Examiner* — Hezron E Williams
*Assistant Examiner* — Alexander Mercado

(57) ABSTRACT

A device, system and method for sampling sample material for an analyte including a receiving swab, wherein at least a portion of the receiving swab is compressible; a sensor for sensing the analyte; and a casing, wherein the casing at least partially encloses the receiving swab and the sensor and allows for a transfer of sample material received by the receiving swab to the sensor along a transfer path inside of the casing. The compressible portion of the receiving swab is located inside the casing, wherein by compressing the compressible portion, the transfer path is closable towards the outside of the device.

12 Claims, 3 Drawing Sheets

(56) References Cited

U.S. PATENT DOCUMENTS

| | | |
|---|---|---|
| 6,375,896 B1 | 4/2002 | Wuske et al. |
| 7,098,040 B2 | 8/2006 | Kaylor et al. |
| 2002/0146346 A1* | 10/2002 | Konecke ............... 422/56 |
| 2004/0171173 A1 | 9/2004 | Eckermann et al. |
| 2004/0184954 A1 | 9/2004 | Guo et al. |
| 2006/0013738 A1 | 1/2006 | Ramsey |
| 2006/0018800 A1 | 1/2006 | Slowey et al. |
| 2007/0239069 A1 | 10/2007 | Guirguis |

FOREIGN PATENT DOCUMENTS

| | | |
|---|---|---|
| WO | 9906827 A2 | 2/1999 |
| WO | 02082040 A2 | 10/2002 |
| WO | 2007016692 A1 | 2/2007 |
| WO | 2007087261 A2 | 8/2007 |

* cited by examiner

SAMPLING DEVICE AND SAMPLING METHOD

FIELD OF THE INVENTION

The present invention relates to a device for sampling sample material for an analyte, to a method of sampling sample material for an analyte, and to a swab.

BACKGROUND OF THE INVENTION

WO 02/082040 A2 discloses a "one-device" system for testing constituents in fluids. The collecting/test device of WO 02/082040 A2 comprises a collection/extraction area and a detection area. The collection extraction area comprises an absorbent pad which is used to collect a sample for testing. A cap is then placed over the collection/extraction area which is provided with pressure heads, which press sample material through micro-sample pores into the core of the collection/extraction area, from where the sample material eventually reaches the detection area.

SUMMARY OF THE INVENTION

It is an object of the present invention to provide a device and a swab for sampling sample material for an analyte and a method of sampling sample material for an analyte which allows in particular for point of care applications (POC applications) or for time sensitive applications with a small number of separate parts and a small number of handling steps, without relying on instruments which are bulky and/or complicated to use.

In a first aspect of the present invention a device for sampling sample material for an analyte is presented that comprises a receiving swab, wherein at least a portion of the receiving swab is compressible; a sensor for sensing the analyte and a casing, wherein the casing at least partially encloses the receiving swab and the sensor and allows for a transfer of sample material received by the receiving swab to the sensor along a transfer path inside of the casing; wherein the compressible portion of the receiving swab is located inside the casing, wherein by compressing the compressible portion the transfer path is closable towards the outside of the device.

In a further aspect of the present invention a system for sampling sample material for an analyte is presented, comprising a device for sampling sample material for an analyte according to the present invention and a receiving apparatus for at least partially accommodating the device, wherein the receiving device comprises a squeezer for compressing the compressible portion of the receiving swab.

In a yet further aspect of the present invention a method for sampling sample material for an analyte is presented, comprising the steps of providing a device for sampling sample material for an analyte according to the present invention, receiving sample material by means of a receiving swab; and compressing a compressible portion of the receiving swab, thereby closing a transfer path from the receiving swab to a sensor for sensing the analyte towards the outside of the device.

A further aspect describes a swab for receiving fluids comprising an outside portion, a compressible portion and an inside portion, whereby the swab abuts on a fluidic channel, the fluidic channel receiving fluid from the swab.

The present invention is based on the insight that a receiving means for receiving sample material from the outside of a device for sampling may further be used as a closing means for enclosing at least a part of the received material inside the device where the enclosed material may then be analyzed, including any further processing which may be provided prior to the actual analysis such as a conditioning of the sample material (including but not limited to dilution, solution or (a) particular chemical reaction(s)).

In others words, the present invention provides a sampling device, which may be disposable, including a pad which is at least partial compressible (or even elastic) and which therefore may be squeezed by mechanical action, essentially closing a part of the pad from the outside world, wherein this pad is connected to a fluidic channel or path leading to a sensor. As this pad is an integral part of the (disposable) device, there is only one element to be handled by the user during the sampling.

Furthermore, a simple instrument which acts on the sampling device (which may be disposable) by mechanical actions when the sampling is inserted into the instrument may be provided, thus providing a system for sampling including the sampling device and the instrument. For instance, but not to exclude other methods, the mechanical actions on the sampling device (i.e. the compressing of the receiving swab) may be caused by cantilever actions induced by the sampling device itself during insertion.

The present invention enables a point of care test with little handling and with use of a simple and small instrument by only having to insert the device for sampling as a diagnostic device into an instrument or actuating the device for sampling manually, and thereafter reading the result after the test is ready. In particular if the device for sampling is used together with an instrument for actuating, the instrument may automatically carry out a number of mechanical actions, thereby controlling a sequence of events in the disposable device with a particular reliability.

The use of diagnostics at the point of care can have benefits in the sense of relating a diagnostic result to an immediate therapeutic action. Other benefits may include that the result is available rather quickly, for example right on the spot, wherein one does not have to rely on sending a specimen to a laboratory.

It is to be noted that the present invention is not limited to point of care applications or to time sensitive applications. An example of a time sensitive application is the testing for drugs in traffic, having the capability of removing an impaired person from the traffic immediately. In the strictest sense such a testing for drugs of abuse in traffic is not a point of care application for the subject giving the sample. However, due to the constraints of such a traffic control, such testing may at least be considered as a time sensitive application. Furthermore, in the sense that the public is defended against abusers, the testing may also be considered to be a POC application.

In addition to point of care applications or time sensitive applications, the present invention may also be employed in a laboratory, thus replacing conventional laboratory means for testing.

Preferred embodiments of the invention are defined in particular in the dependent claims. It shall be understood that the device of claims 1 to 10 and the system of claims 11 to 13 have similar and/or identical preferred embodiments as defined in the dependent claims.

According to a preferred embodiment of the present invention, the receiving swab is porous. A porous receiving swab is particularly advantageous since it provides a sufficient capability of taking in sample material (inside the pores) together with an adjustable compressibility (due to the size of the pores) for providing a closure to the outside. A porosity in the range of 40% to 80% is preferred, wherein a porosity in the range of 60% to 80% is particularly preferable.

According to a further preferred embodiment of the present invention, at least the compressible portion is resilient. A resiliency of the compressible portion makes it possible to the reverse the compression process, which may for example be necessary in a case where after compressing the compressible portion it is found out that the amount of received sample material is not sufficient and additional sample material is to be received.

However, it is noted that a resiliency of the compressible portion is not an essential feature as the compressible portion may also be provided as being compressible without the capability of returning to an in-compressed state.

According to another preferred embodiment of the present invention the device for sampling further comprises a container for a conditioning fluid which is connectable to the transfer path. The provision of a container for conditioning fluid allows for a conditioning of the received sample material without the need for a further step of receiving conditioning fluid from the outside of the device for sampling. Preferred examples of a conditioning fluid include an elution buffer for recovering the analyte from the receiving swab and/or an assay buffer for conditioning the sample to perform an assay.

According to a preferred embodiment of the present invention, the container is a blister containing the conditioning fluid and is rupturable for discharging the fluid to the transfer path. A blister may be produced easily and inexpensive while providing for a desired and defined breaking point of the blister for expelling the fluid into the transfer path.

According to a further preferred embodiment of the present invention, the device for sampling further comprises a mixing area in the transfer path, comprising porous mixing material and/or one or more microfluidic mixers. In addition to any mixing which may take place inside the transfer path, in particular in the area of the transfer path between the receiving swab and the sensor, the mixing area ensures a predetermined mixing of the sample material and the conditioning liquid prior to the arrival at the sensor. In addition, the mixing area might have a filter characteristic, for example preventing particles from reaching the sensor. The one or more microfluidic mixers may, for example, be based on folding and diffusion of the liquids.

According to another preferred embodiment of the present invention, the receiving swab comprises an outside portion, the compressible portion and an inside portion, wherein the inside portion is part of the transfer path and wherein the mixing area is larger than the inside portion. The inside portion of the receiving swab initially contains most of the sample material which eventually reaches the sensor. Thus, in order to provide a desired amount of mixing, the mixing area is provided with a volume which is greater than that of the inside portion of the receiving swab.

According to a preferred embodiment of the present invention, the transfer path includes a microfluidic channel. In addition to the advantage that only minute amounts of sample material is needed for filling a microfluidic channel, the particular behavior of fluids in microfluidic channels may advantageously used.

According to a further preferred embodiment of the present invention, the device for sampling further comprises a wetting sensor for determining a wetting status of the receiving swab. By providing a wetting sensor, a wetting detector or a sample adequacy indicator, in particular behind the receiving swab (i.e. between the receiving swab and the sensor), it is assured that a sufficient amount of sample material is collected. This may in particular be relevant in order to prevent fraud.

According to another preferred embodiment of the present invention, the device for sampling further comprises an interface for reading out the sensor. In correspondence thereto, according to a preferred embodiment of a system for sampling of the present invention, the device for sampling comprises a device interface for reading out the sensor and the receiving apparatus includes an apparatus interface adapted to be coupled with the device interface for reading out the sensor. The interface may include an electrical interface and/or an optical interface. The interface allows for reading out any result of the sensing or sampling automatically, thus further reducing an interaction between the device or method for sampling and the user, which may cause errors.

According to a further preferred embodiment of a system for sampling of the present invention, the squeezer of the receiving apparatus is adapted to be actuated by means of cantilever action caused by an insertion of the device for sampling into the receiving apparatus. The insertion of the device for sampling itself results in the start of the compression of the compressible portion of the receiving swab. Thus, an additional actuation by a user is not necessary, resulting in a reduction of processing steps to be performed by the user.

According to another preferred embodiment of a method of sampling according to the present invention, the method of sampling further comprises discharging sample material from the receiving swab towards the sensor after closing the transfer path by compressing the receiving swab, and/or discharging a conditioning fluid from a container connected to the transfer path for transferring sample material from the receiving swab to the sensor. The sample material contained in the inside portion of the receiving swab may be transported or driven to the sensor due to a compression of the receiving swab (i.e. due to an expelling of the sample material from the inside portion) and/or due to a flow of conditioning material which "picks up" sample material and takes the sample material to the sensor. The active actuation by any one of these means of transport or a combination thereof makes sure that the sample material is brought to the sensor in a sufficient amount for detecting the analyte.

Further, it is to be noted that, according to the present invention, although it is defined that the receiving swab comprises a compressible portion, the present invention also includes embodiments in which the (complete) receiving swab as such is compressible or even resilient.

A device for sampling according to the present invention may include in particular a biosensor based on a magnetic label assay. A particular advantage of such a biosensor over sensors like a simple test strip is the possibility of reading out the biosensor electronically.

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Similar or corresponding elements of the following embodiments illustrated in the Figures are indicated by similar or corresponding reference signs.

Figure 1:
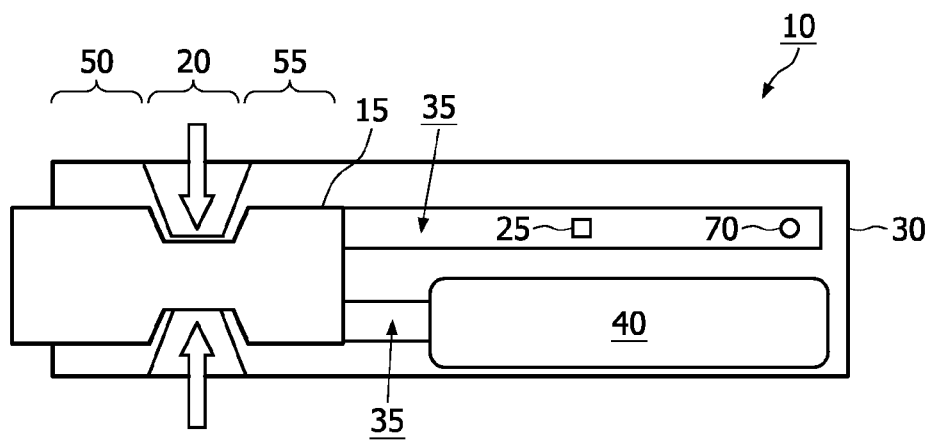
FIG. 1 shows a schematic illustration of a device for sampling according to first embodiment of the present invention.

FIG. 1 shows a schematic illustration of a device for sampling according to first embodiment of the present invention. The device for sampling according to this first preferred embodiment is formed integrally, i.e. only one piece of equipment is to be handled by a user in order to collect sample material. This also applies to the further embodiments described in the following. However, it has to be noted that a device for sampling according to the present invention may also be constructed by combining two or more parts, e.g. by connecting a receiving portion and a sensor portion, in a modular way.

The device 10 for sampling comprises a receiving swab 15, a sensor 25 and a blister 40 containing a conditioning liquid, which are included in a single housing 30. The receiving swab 15 and the sensor 25 are in fluid connection to a transfer path 35 in form of a microfluidic path. The conditioning liquid is contained in the blister 40 and may be propelled from the blister 40 by applying pressure to the blister 40 in order to provide for a rupture (not shown) through which the conditioning liquid may reach the transfer path 35. Merely an outside portion 55 of the receiving swab 15 is provided at the outside of the housing 30 in order to be able to receive sample material like saliva, blood, urine or any other material to be sampled. A central portion 20 of the receiving swab is compressible. In FIG. 1 this compressible portion 20 is shown in a compressed state, wherein the compression of this portion provides a blocking and closes the transfer path 35 from the outside of the device 10 for sampling. Preferably, in order to provide a sufficient wetting of the complete receiving swab 15, the receiving swab 15 is brought into contact with the sample source with the compressible portion 20 in an uncompressed state (not shown).

Upon applying the device 10 for sampling to the mouth of a person, the rather small receiving swab 15 is filled rapidly and therefore the sample taking is quick and comfortable. Next the device 10 is inserted into a simple (e.g. handheld) instrument (not shown in FIG. 1) and by mechanical cantilever action causing a compression of the compressible portion 20 of the receiving swab 15, an inside portion 55 of the swab 15 is closed from the outside world. Thereafter, a second cantilever action is carried out and thereby the blister 40 is punctured and the (buffer) liquid is propelled towards the swab and the sample is chased out of the inside portion 55 of the swab 15 being an integral part of the microfluidic path 35 and thereby transported to the sensor 25 provided in a detection area of the device 10 for sampling. The puncturing or rupturing of the blister 40 is carried in such a manner that no liquid escapes from the microfluidic system 35.

However, the device 10 shown in FIG. 1, as well as those described with respect to the other embodiments, is not limited to being used together with an instrument for squeezing or compressing the compressible portion 20 and for rupturing the blister 40. The device 10 may also be used manually, e.g. by providing a suitable means for compressing the compressible portion 20 (such as a clamp) for ensuring a closure of the transfer path 35 from the outside and by manually pressing the blister for a (controlled and predetermined) rupture. A compressing means is preferable over even simpler direct compression of the compressible portion 20 by a user, as the compressing means may be adapted to provide a predetermined pressure force which is sufficient for closing the transfer path 35 from the outside.

According to the present embodiment, the sensor 25 is a test pad comprising a reactant indicating the presence of an analyte in the mixture of saliva (as an example of sample material) and conditioning liquid by a color change. Thus, the casing is adapted for allowing a user an observation of the test pad by means of a transparent portion of the casing. However, according to another embodiment the casing may also be adapted to be removed or opened in order to allow for an inspection of the test pad 25. However, it has to be noted that the particular kind of sensor is not an essential feature of the respective embodiments described here. Any sensor or sensor system provided in a particular embodiment of the present invention may be exchanged with any sensor or sensor system of another embodiment according to the present invention. Furthermore, it is noted that the present invention is not limited to the provision of a single sensor or sensor system and a number of sensors and/or sensor systems may be provided together, detecting the same or different analytes.

The transfer path 35 is further provided with an air-vent 70 as an example of a venting element, arranged beyond the sensor 25 (as seen from the receiving swab 15), which allows for an escape of air (on any other gas which might be provided inside the device instead of or in addition to air) displaced by the flow of conditioning liquid together with sample material inside the transfer path 35.

A number of different implementations of a venting element may be used. In particular, the venting element might include a geometrical liquid stop. An alternative or additional option is the provision of a hydrophobic liquid stop for stopping water/aqueous liquid from exiting through the venting element. In case the material inside the device, i.e. the sample material and/or the conditioning liquid, is not water-based, a liquid stop corresponding to the hydrophobic liquid stop may be used. In a case where any exit of material from the venting element is not of concern, the venting element may also be just a simple opening without any restraining feature in regard of the sample material and/or the conditioning liquid. However, additional provisions may be taken in order to prevent a fraudulent introduction of material through the venting element.

The above discussion also applies to the venting elements provided in the further embodiments described below. However, it is noted that a venting element may also be omitted as the air inside the transfer path might be compressed to some extent without any need for a venting element. Further, instead or in addition to a venting element, a compartment might be provided in fluid connection to the transfer path, wherein the inner volume of the compartment is larger than the inner volume of the transfer path (preferably one or more orders of magnitude larger). Air (or other gas) which is displaced due to the flow of liquid through the transfer path is moved to the compartment, wherein, due to the larger volume of the compartment, this movement results in only a minor increase in pressure of the air (or other gas) which does not hinder the flow through the transfer path. Another option is the provision of a looped transfer path, i.e. that the displace air (or other gas) is directed to the original location of the liquid causing the displacement.

Figure 2:
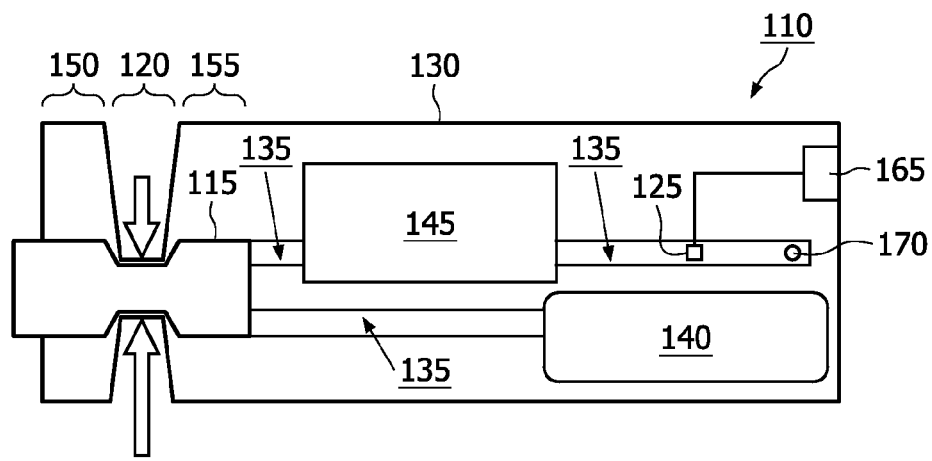
FIG. 2 shows a schematic illustration of a device for sampling according to a second embodiment of the present invention.

FIG. 2 shows a schematic illustration of a device for sampling according to a second embodiment of the present invention. Again, also the device for sampling according to this second embodiment is formed as an integral device. As the device according to the first embodiment described above referring to FIG. 1 and the devices according to the following embodiments, the device for sampling according to the second embodiment is provided as a disposable device. However, as it will be appreciated by the skilled reader, the device for sampling according to the present invention may also be provided as a reusable device. However, as the costs for producing a device according to the present invention are likely to be small in comparison to the effort needed for reusing the device for sampling, the provision of a disposable device according to the present invention is preferred.

Similar to the device illustrated in FIG. 1, the device 110 for sampling according to the second embodiment comprises a receiving swab 115 having an outside portion 150, a compressible portion 120 and an inside portion 155, a sensor 125 and a blister 140 containing a conditioning liquid, which are included in a single housing 130. Basically, these elements correspond to those of the device shown in FIG. 1. Thus a further description thereof may be omitted here. Similar to FIG. 1, the compressible portion 120 is shown in a compressed state.

Further, the device 110, which may also be referred to as a cartridge for a sensing (in particular biosensing) application, comprises in addition to the features of the device illustrated in FIG. 1 a porous mixing pad 145, which is larger than he inside portion 155 of the receiving swab 115 which is closed from the outside world by means of the compression of the compressible portion 120. Yet further, the device 110 for sampling comprises an interface 165 connected to the sensor 125.

The porous mixing pad 145 is provided in the transfer path 135 of the device 110 for sampling between the inside portion 155 of the receiving swab 115 (functioning as a source for sample material inside the device 110) and the sensor 125 in order to allow for a desired mixing of the sample material, e.g. saliva, with the conditioning liquid provided in the blister 140. Upon rupturing of the blister 140 the conditioning liquid is propelled towards the inside portion 155 and chases the saliva (as an example of sample material) from the inside portion 155 to the mixing pad 145. Inside the mixing pad 145 the conditioning liquid is mixed with the saliva, thus providing desired properties (like viscosity) of the mixture of sample material (in this case saliva) and conditioning liquid. This mixture then further progresses to the sensor 125 which is designed to be read-out by means of the interface 165. This interface 165 may comprise an electrical interface or an optical interface or otherwise. The interface 165 and the sensor 125 together form a sensor system. The skilled person is well familiar with such sensor systems. Thus, a detailed description thereof may be omitted here. As indicated above, the sensor system including the sensor 125 and the interface 165 of the second embodiment may be replaced by a simple sensor as illustrated and described with respect to the above first embodiment. Similar to the embodiment illustrated in FIG. 1, the transfer path 135 provided with a venting element 170.

As the particular implementation of the sensor function is not essential to the present invention, in comparison to the above first embodiment, the main difference of the second embodiment is that the additional porous pad is provided. The operation of second embodiment is essentially the same as that of the first embodiment with this exception that the sample is mixed in the mixing pad with a part of the liquid buffer (conditioning liquid), thereby conditioning the sample material. However, in regard of the actions to be taken from the outside (i.e. the compression of the compressible portion and the rupturing of the blister), the handling is virtually identical for both, the first and the second embodiment. As in the case of the first embodiment, the liquid mixture of sample material and conditioning liquid (which, in the case of the second embodiment, is additionally filtered due to the porosity of the mixing pad) detection area where the sensor-interaction take place and the relevant species (i.e. the analyte) reacts with (the surface of) the sensor. The result of such a reaction may then, according to the second embodiment, be read out by means of the interface.

Figure 3:
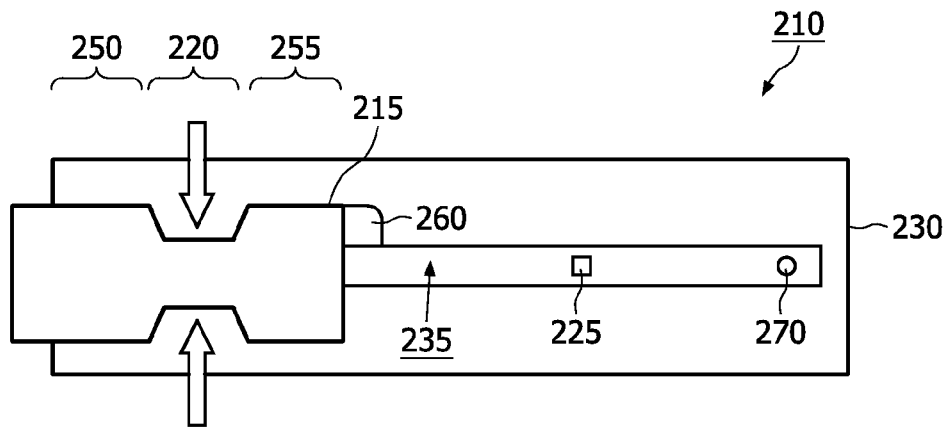
FIG. 3 shows a schematic illustration of a device for sampling according to a third embodiment of the present invention.

FIG. 3 shows a schematic illustration of a device for sampling according to a third embodiment of the present invention. The third embodiment of the present invention illustrated in FIG. 3 includes a device 210 for sampling, the construction of which is somewhat simpler in comparison to the first and second embodiment described above.

Again similar to the above embodiments illustrated in FIGS. 1 and 2, the device 210 for sampling according to this third embodiment comprises a receiving swab 215, having an outside portion 250, a compressible portion 220 and an inside portion 255, and a sensor 225, which are included in a single housing 130, wherein the receiving swab 215 and the sensor 225 are in fluid connection by means of the transfer path 235 which includes a venting element 270. In contrast to the first and second embodiment, the device 210 does not include a blister or any other source for a conditioning liquid. However, the device 210 is further provided with a wetting sensor adapted for detecting whether or not a predetermined amount of wetting of the receiving swab 215 is achieved. The device 210 for sampling according to this third embodiment is particularly useful in cases where an additional conditioning of the sample material is not necessary.

Further, it is noted that, according to the present invention, an even simpler embodiment may be provided (not shown). The wetting sensor 260 may be omitted, provided that during operation of such a simple implementation measures are taken to ensure a sufficient wetting of the receiving swab (i.e. to ensure that a sufficient amount of sample material is taken up by the receiving swab).

The (small) receiving swab 215 is filled rapidly and therefore the sample taking is quick and comfortable, similar to the case of the first embodiment. A sufficient intake of sample material corresponding to a predetermined wetting of the receiving swab 214 is detected by means of the wetting sensor 260. Then, again similar to the first embodiment, the device 215 (which may be disposable) is inserted into a simple (handheld) instrument, wherein for instance by a mechanical cantilever action a part (the inside portion 255) of the swab 215 is closed from the outside world due to the compression of the compressible portion 220. By the same squeezing action providing the compression of the compressible portion 220 a part of the content of the swab 215 is propelled into the microfluidic path 235 up to the detection area, where the sensor 225 is located. In this embodiment the size of the receiving swab 215 is be dimensioned such that there is sufficient volume of the content propelled in the micro-fluidic channel 235 and the sensor 225 is wetted as needed.

Depending on the dimensions of the elements of the device 210 for sampling, the compression of the compressible portion 220 of the receiving swab 215 may be sufficient to drive enough sample material to the sensor 225. However, in order to increase the amount of sample material driven to the sensor 225, the inside portion 255 of the receiving swab may also be compressed as it is indicated in FIGS. 4a-4d.

FIGS. 4a-4d show schematic illustrations of different stages of a compression of a receiving swab according to a further aspect of the present invention. According to one aspect of the present invention, as indicated above, not only the compressible portion of a receiving swab is compressed or squeezed for enclosing the inside portion of the receiving swab from the outside, but also the inside portion of the receiving swab is compressed or squeezed in order to drive sample material from the receiving swab to the transfer path and ultimately to the sensor.

Figure 4A:
FIGS. 4a-4d show schematic illustrations of different stages of a compression of a receiving swab according to a further aspect of the present invention.
Figure 4B:
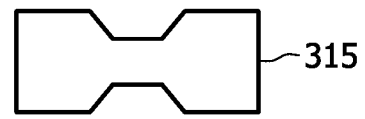
Figure 4C:
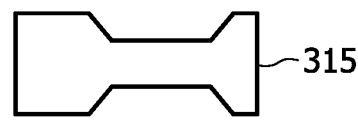

In FIGS. 4a-4d only the receiving swab is shown, the other elements of the present invention are omitted for sake of clarity. In FIG. 4a the receiving swab 315 is shown in a state in which the swab is not (yet) compressed. It is to be noted that the general shape of the receiving swab according to the present invention is not limited to the particular rod-like shape illustrated in the figure. The receiving swab may have any shape or configuration allowing for taking up sample material. The state of the receiving swab 315 which is illustrated in FIG. 4b corresponds to those of the receiving swabs illustrated in FIGS. 1 to 3, i.e. a compressible mid-portion is compressed and closes any fluid connection from the inside portion (provided on the right side in FIGS. 4a-4d) to the outside or outside portion (provided on the left side in FIGS. 4a-4d), which is at least partially exposed to the outside. Thus, sample material contained in the inside portion is confined to the inside of the device for sampling (further elements of which are not shown in FIGS. 4a-4d). In FIG. 4c the compression progresses from the state illustrated in FIG. 4b to the state of complete compression of both, the compressible portion of the receiving swab 315 (acting as a closure towards the outside) and the inside portion of the receiving swab 315. In the state illustrated in FIG. 4d the receiving swab 315 is compressed, whereby sample material originally contained inside the receiving swab 315 (more particularly inside the inside portion and to some extent inside the compressible portion) is removed or expelled from the receiving swab towards the transfer path (not shown) leading to the sensor (not shown).

Figure 4D:
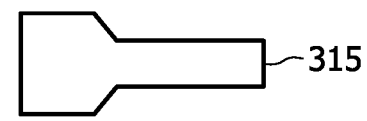

However, different from the stages illustrated in FIGS. 4c and 4d, the compression of the inside portion of the receiving swab may also be provided separately from that of the compressible portion.

It has to be noted that the additional compression of (a part of) the inside portion of the receiving swab is not limited to an embodiment like the above described third embodiment. Such a measure to increase the amount of sample material which is removed from the receiving swab and transported to the sensor may also be taken in regard of other embodiments of the present invention, as for example those illustrated in FIGS. 1 and 2 or described above or in the following.

Figure 5A:
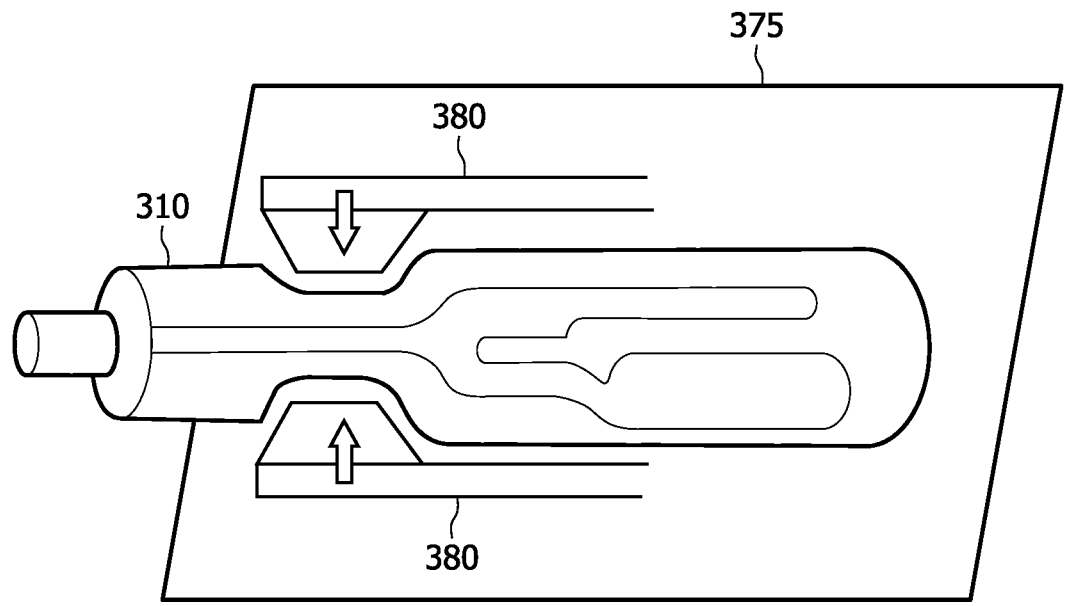
FIGS. 5a, 5b show schematic illustrations of a system for sampling according to the present invention.
Figure 5B:
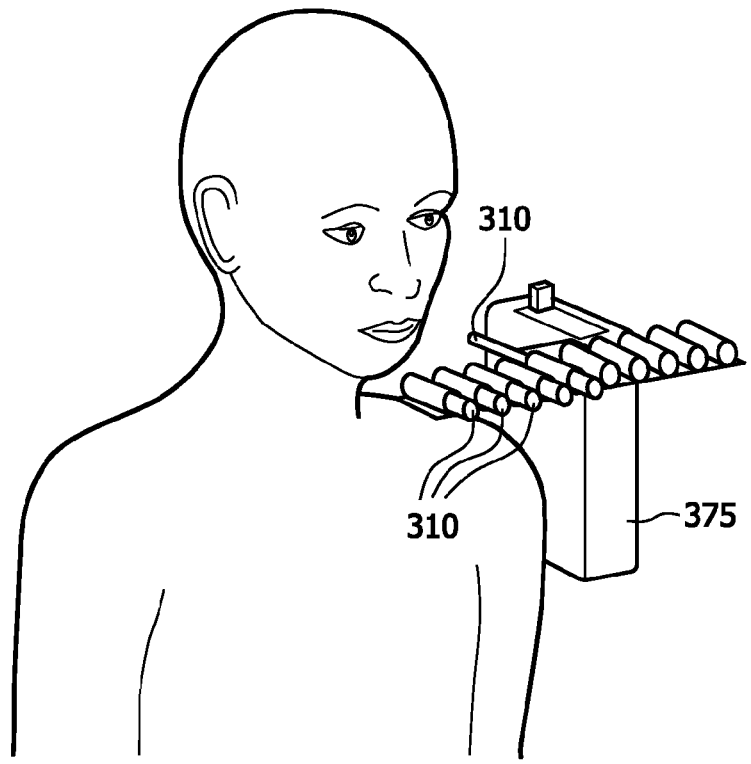

FIGS. 5a and 5b show schematic illustrations of a system for sampling according to the present invention.

FIG. 5a schematically shows a device 310 for sampling according to the present invention, similar to the device according to the embodiment illustrated in FIG. 1, which is inserted in a receiving apparatus 375. The receiving apparatus 375 is provided with a pair of squeezers 380 which provide a compression force for compressing the compressible portion of the device 310 (as indicated by the arrows).

FIG. 5b schematically shows a system including a plurality of devices 310 according to the present invention together with a receiving apparatus 375. The devices 310 are provided as cartridges integrated in a belt for being delivered to the receiving apparatus 375. Thus, a number of devices 310 may be fed automatically to the receiving apparatus 375, thus allowing for a number of sampling processes to be performed rapidly after one after the other.

Figure 6:
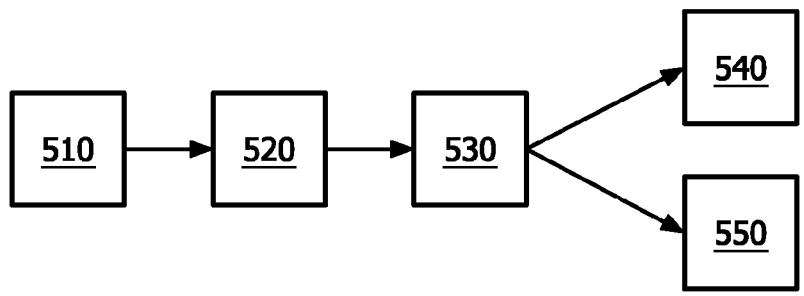
FIG. 6 shows a schematic flow chart illustrating a method for sampling according to a further embodiment of the present invention.

FIG. 6 shows a schematic flow chart illustrating a method for sampling according to a further embodiment of the present invention. According to a particular embodiment, the method for sampling according to the present invention includes a step 510 of providing a device for sampling sample material for an analyte according to the present invention, for example according to one of the embodiments described herein. In step 520 sample material is received by means of the receiving swab of the device, whereafter a compressible portion of the receiving swab is compressed in step 530, thereby closing a transfer path from the receiving swab to a sensor for sensing the analyte towards the outside of the device. Further, either as alternatives or in parallel the steps of discharging (540) sample material from the receiving swab towards the sensor after closing the transfer path by compressing the receiving swab and/or of discharging (550) a conditioning fluid from a container connected to the transfer path for transferring sample material from the receiving swab to the sensor are provided. However, as indicated above, the steps 540 and 550 are not mandatory and may be omitted. Eventually, the sample material reaches the sensor, where the analyte or its absence is detected.

According to a particular further embodiment of the present invention, a porous pad is used as collection device, being an integral part of an IVD device (in vitro diagnostics device, not shown in the Figures, however similar to the embodiment illustrated in FIG. 1 or 3). The pad has an elastic property allowing mechanical squeezing of the pad in such a manner that at least a part of the pad is closed from the outside world, wherein this part of the pad becomes a portion of a microfluidic path within the device (although the elasticity of the pad material is not essential, as being compressible is sufficient).

Sample material contained in this part of the pad may be propelled into the microfluidic path in two alternative and/or complementary manners, i.e. the sample material is wetted by a liquid buffer and as such propelled to a detection area of the device for sampling and/or due to the squeezing action at least a part of the sample material contained in the part of the pad is propelled to the detection area.

The mechanical squeeze action may be carried out by a simple instrument. One benefit is that the disposable IVD product consists of only one integral part, wherein the necessary handling is reduced to taking up a sample in the pad and inserting the disposable IVD device into the instrument actuating the compression of the pad. This allows, for instance, in particular for a point of care application in the field.

As a further modification of the above embodiment (similar to the embodiment illustrated in FIG. 2), an additional mixing feature may be integrated into the device for sampling, being, for example, a larger pad in the microfluidic path. When the sample is chased out of the first pad (used for taking up the sample material) by the liquid buffer, both, sample material as well as liquid buffer, will enter the second pad (used for mixing). This second pad is a percolating system having different pore sizes and therefore the sample material entering the pad together with the liquid buffer is distributed well over the pad. Eventually, the mixed liquid will be transported to the detection area.

In the foregoing, the present invention has been further illustrated by means of particular embodiments, wherein referral is taken to saliva as an exemplary sample material. Saliva is a usually difficult sample material, in particular because its properties are usually not very well defined. For example, its mechanical properties (such as viscosity) may vary from person to person and it may also depend on the time of day, whether the person to be tested has just eaten/drunk something etc. For this reason the saliva sample is frequently diluted with a buffer to improve a consistency of the results obtained. A main problem with this dilution is that it conventionally requires an operator to take a number of steps, including a placement of the sample into a container with buffer material, shaking the buffer material together with the sample material for mixing of these and the applying of the diluted sample material (together with the buffer material) in a sample cartridge for testing. Additionally, a considerable number of tests require quite a large sample volume, which can easily take more than a minute to collect. In particular for POC applications a long sample collection time and a complicated handling are not acceptable.

However, it has to be noted that the present invention is suitable for an analysis of liquid sample material in general, including but not limited to saliva, blood and urine. Furthermore, provided that a species of interest is provided in a suitable form, e.g. by exposing to a liquid elution buffer, even gaseous or solid sample materials may be analyzed.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. A device for sampling a sample material for an analyte, the device comprising:
   a swab including an outside portion for receiving the sample material, a compressible portion for holding the sample material, and an inside portion integral with the compressible portion; and
   a casing capable of forming a compressed state or an uncompressed state, the casing including:
      a transfer path for transporting the sample material, wherein the inside portion of the swab is part of the transfer path, and
      an opening configured to receive the inside portion of the swab and compress at least one of the compressible portion and the inside portion of the swab,
      wherein changing the casing from the uncompressed state to the compressed state causes the sample material to flow into the inside potion, a portion of the sample material to be enclosed from an outside environment, and the sample material to be transferred into the transfer path, and
      a sensor positioned along the transfer path for sensing the analyte in the transported sample material.

2. The device according to claim 1, wherein the swab is porous.

3. The device according to claim 1, wherein the compressible portion is resilient.

4. The device according to claim 1, wherein the transfer path further includes a blister container for discharging a conditioning fluid to the transfer path.

5. The device according to claim 1, wherein a mixing area connected to the transfer path comprises a percolating system having different pore sizes.

6. The device according to claim 1, wherein the transfer path includes a microfluidic channel.

7. The device according to claim 1, further comprising:
   a wetting sensor adjacent the inside portion of the swab and the transfer path for determining whether a predetermined amount of wetting of the receiving swab is achieved.

8. A system for sampling a sample material for an analyte, comprising:
   a sampling device comprising:
      a swab including an outside portion for receiving the sample material, a compressible portion for holding the sample material, and an inside portion integral with the compressible portion; and
      a casing capable of forming a compressed state or an uncompressed state, the casing including:
         a transfer path for transporting the sample material, wherein the inside portion of the swab is part of the transfer path,
         an opening configured to receive the inside portion of the swab and compress at least one of the compressible portion and the inside portion of the swab, and
         a sensor positioned along the transfer path for sensing the analyte in the transported sample material; and
   a receiving apparatus including a squeezer for changing the casing from the uncompressed state to the compressed state, thereby enclosing a portion of the swab from an outside environment and transferring the sample material towards the sensor through the transfer path.

9. The system according to claim 8, wherein the casing of the sampling device includes an electrical or optical interface for reading out the sensor.

10. The system according to claim 8, wherein the squeezer changes the state of the casing by cantilever action caused by an insertion of the sampling device into the receiving apparatus.

11. A method of sampling a sample material for an analyte, the method comprising acts of:
   providing a device for sampling sample material for an analyte, the device comprising:
      a swab having an outside portion at least partially exposed to an outside environment, a compressible portion for holding the sample material, and an inside portion integral with the compressible portion, and
      a casing capable of forming a compressed state or an uncompressed state, the casing including:
         a transfer path for transporting the sample material, and
         an opening configured to receive and compress the compressible portion of the swab, and
         a sensor positioned along the transfer path for sensing the analyte in the transported sample material;
   receiving the sample material on the compressible portion of the swab;
   inserting the swab into the opening;
   changing the casing from the uncompressed state to the compressed state, thereby closing any fluid connection from the inside portion of the swab to the outside portion of the swab and transferring the sample material from the compressible portion of the swab to the transfer path;
   sensing the analyte in the transported sample material.

12. The method according to claim 11, further including:
    transferring a conditioning fluid from a blister connected to the transfer path by rupturing the blister.

* * * * *